United States Patent [19]

Naito et al.

[11] Patent Number: 4,845,257

[45] Date of Patent: Jul. 4, 1989

[54] 4-HALOGENO-2-OXYIMINO-3-OXOBUTYRIC ACIDS AND DERIVATIVES

[75] Inventors: Kenzo Naito, Kyoto; Yukio Ishibashi, Osaka, both of Japan

[73] Assignee: Takeda Chemical Industries, Ltd., Osaka, Japan

[21] Appl. No.: 50,332

[22] Filed: May 18, 1987

[30] Foreign Application Priority Data

May 21, 1986 [JP]  Japan .................................. 61-116673

[51] Int. Cl.$^4$ .................................................. C07F 7/10
[52] U.S. Cl. ...................................... 556/418; 556/415; 560/147; 560/168; 548/110
[58] Field of Search ................ 556/418, 415; 560/147, 560/168; 548/110

[56] References Cited

U.S. PATENT DOCUMENTS

| | | | |
|---|---|---|---|
| 3,560,543 | 4/1971 | Plueddemann | ................... 556/418 X |
| 3,833,633 | 9/1974 | Owen et al. | ...................... 556/418 X |
| 3,856,848 | 12/1974 | Smithwick | ....................... 556/418 X |
| 4,554,369 | 11/1985 | Hill et al. | .............................. 556/418 |
| 4,709,067 | 11/1987 | Shibasaki et al. | .................... 556/418 |

FOREIGN PATENT DOCUMENTS

| | | | |
|---|---|---|---|
| 528689 | 7/1981 | Australia | .......................... 556/418 X |
| 0009671 | 4/1980 | European Pat. Off. | ........ 556/418 X |
| 0030294 | 6/1981 | European Pat. Off. | ........ 556/418 X |
| 57-197257 | 5/1982 | Japan | .............................. 556/418 X |
| 60-228486 | 5/1985 | Japan | .............................. 556/418 X |
| 2012276 | 7/1979 | United Kingdom | ........... 556/418 X |
| 2161476 | 1/1986 | United Kingdom | ........... 556/418 X |

OTHER PUBLICATIONS

Chem. Pharm. Bull. 25, pp. 3115-3117 (1977).
Journal Antibiotics, 38, pp. 1738-1751 (1985).
Journal of the chemical Society of Japan 1981, No. 5, pp. 785-803 (English Translation of Relative Portions in the Items "2.9.1" and "3.3.2" at pp. 792 and 798).

*Primary Examiner*—Paul F. Shaver
*Attorney, Agent, or Firm*—Wegner & Bretschneider

[57] ABSTRACT

A method of producing a 4-halo-2-(substituted or unsubstituted)hydroxyimino-3-oxobutyric acid ester or amide, which is a synthetic intermediate of value for the production of cephalosporins containing an aminothiazole group, characterized by reacting a 2-(substituted or unsubstituted)-hydroxyimino-3-oxobutyric acid or an ester or amide thereof with a silylating agent and reacting the resulting novel 2-(substituted)hydroxyimino-3-silyloxy-3-butenoic acid ester or amide with a halogenating agent.

16 Claims, No Drawings

4-HALOGENO-2-OXYIMINO-3-OXOBUTYRIC ACIDS AND DERIVATIVES

The present invention relates to an industrially advantageous method for producing 4-halo-2-(substituted or unsubstituted)hydroxyimino-3-oxobutyric acid esters or amides (hereinafter referred to as objective compound (I)) which are of value as synthetic intermediates, particularly as intermediates for the synthesis of cephalosporin compounds.

Esters and amides of 4-halo-2-(substituted or unsubstituted)hydroxyimino-3-oxobutyric acids are synthetic intermediates of value for the production of cephalosporins containing an aminothiazole group, of which Cefmenoxime is representative. As antibiotics having extended antibacterial spectra, several kinds of aminothiazole-containing cephalosporins have already been sold and used widely in clinical practice, and their chemical structures and pharmacological activities as well as methods for production thereof have been described in the literature such as Angew. Chem. Int. Ed. Engl. 24, 180-202 (1985), J. Antibiot. 38, 1738-1751 (1985) and so on. The objective compound (I) is used for the formation of the aminothiazole moiety in such production processes of the aminothiazole-containing cephalosporins.

The objective compound (I) or its free acid has heretofore been synthesized either by reacting a 2-(substituted or unsubstituted)hydroxyimino-3-oxobutyric acid or an ester or amide thereof (hereinafter referred to as compound (II)) directly with a halogenating agent [Japanese Published Unexamined Patent Application No. 60-228486; GB 2012276-B; EP 30294-A; GB 2161476-A; Chem. Pharm. Bull. 25, 3115-3117 (1977); J. Antibiot. 38, 1738-1751 (1985); Journal of the Chemical Society of Japan 1981 No. 5, 785-803; etc.]or acetalizing a 2-(substituted or unsubstituted) hydroxyimino-3-oxobutyric acid ester, reacting the acetal with a halogenating agent, de-esterifying it and finally hydrolyzing the acetal [EP 9671-A].

However, the above prior art methods for production of objective compound (I) are disadvantageous in that, for example, the reaction must be conducted under strongly acidic conditions, there is co-produced a 4,4-dihalo or 4,4,4-trihalo-2-(substituted or unsubstituted)-hydroxyimino-3-oxobutyric acid ester or amide which is very difficult to separate from objective compound (I), many reaction steps need to be involved, and/or the product yield is poor. Thus, none of the known methods are industrially advantageous The present inventors conducted a comprehensive investigation for developing an industrially advantageous production process for producing objective compound (I) and found that reacting compound (II) with a silylating agent provides a novel compound, 2-(substituted)hydroxyimino-3-silyloxy-3-butenoic acid ester or amide (hereinafter referred to as compound (III)), that reacting this compound (III) with a halogenating agent provides objective compound (I) in high purity and yield in a surprisingly short reaction sequence under mild conditions without use of costly reagents, and that the reaction process is more advantageous than any of the conventional processes for the industrial production of objective compound (I). The present invention has been developed on the basis of the above findings.

The compound (II) mentioned above is a 2-(substituted or unsubstituted)hydroxyimino-3-oxobutyric acid or an ester or amide thereof and as preferred examples of compound (II), there may be mentioned compounds of the formula

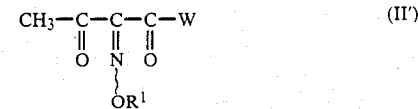
(II')

wherein $R^1$ is a hydrogen atom or an alkyl group which may optionally be substituted; W means $OR^2$, $SR^2$ or

wherein $R^2$ is a hydrogen atom or a hydrocarbon group which may optionally be substituted. In compound (II'), $R^1$ is a hydrogen atom or an alkyl group which may optionally be substituted. As examples of the alkyl group $R^1$, there may be mentioned straight-chain or branched alkyl groups containing 1 to 4 carbon atoms such as methyl, ethyl, propyl, isopropyl, butyl and so on. The alkyl group $R^1$ may have 1 to 2 substituents which may be the same or different, such as carboxyl groups (which may be protected by easily removable protective groups such as p-nitrobenzyl, protective groups such as p-nitrobenzyl, methyl, ethyl, t-butyl, trialkylsilyl or halodialkylsilyl as mentioned below in $R^3$, etc.), cycloalkyl groups of 3 to 6 carbon atoms (for example, cyclopropyl, etc.), heterocyclic groups (for example, nitrogen-containing 5-membered heterocyclic groups such as imidazol-5-yl, etc.) and so on. As examples of said alkyl group which may optionally be substituted, as represented by $R^1$, there may be mentioned methyl, ethyl, cyclopropylmethyl, imidazol-5-ylmethyl, t-butoxycarbonylmethyl, 1-t-butoxycarbonyl-1-methylethyl and so on. Preferred examples of the group $R^1$ include a hydrogen atom and a $C_{1-4}$ alkyl which may optionally be substituted with carboxyl or a protected carboxyl group. The group W means $OR^2$, $SR^2$ or

wherein $R^2$ is a hydrogen atom or a hydrocarbon group which may optionally be substituted. As examples of the hydrocarbon group represented by $R^2$, there may be mentioned straight-chain or branched alkyl groups of 1 to 6 carbon atoms such as methyl, ethyl, propyl, isopropyl, butyl, isobutyl, tert-butyl, pentyl, tert-pentyl, hexyl, etc., alkenyl groups of 2 to 4 carbon atoms such as vinyl, allyl, etc., aryl groups of 6 to 10 carbon atoms such as phenyl, naphtyl, etc., and aralkyl groups of 7 to 10 carbon atoms such as phenyl-$C_{1-4}$ alkyl(such as benzyl, phenylethyl, etc.), and so on. The hydrocarbon group represented by $R^2$ may have 1 to 2 substituents which may be the same or different, such as $C_{1-4}$ alkylsulfonyl groups (such as methylsulfonyl, etc.), $C_{1-4}$ alkylsulfinyl groups (such as methylsulfinyl, etc.), $C_{1-4}$ alkylthio groups (such as methylthio, etc.), $C_{3-6}$ cycloalkyl groups (such as cyclopropyl, cyclobutyl, cyclohexyl, etc.), hydroxyl, nitro, $C_{1-4}$ alkoxy groups (such as methoxy, ethoxy, etc.), di-$C_{1-4}$ alkylamino groups (such as dimethylamino, diethylamino, etc.) and so on. Where $R^2$ represents an aryl group or an aralkyl group, it may have 1 to 2 substituents which may be the same or different, such as $C_{1-4}$ alkyl groups (e.g. methyl, ethyl, propyl, butyl, t-butyl, etc.) and other groups. Examples of the hydrocarbon group which may optionally be substituted, as represented by $R^2$, include substituted or unsubstituted aliphatic hydrocarbon groups such as methyl, ethyl, propyl, isopropyl, butyl, isobutyl, tert-butyl, pentyl, tert-pentyl, hexyl, 1 cyclopropylethyl, allyl, methylsulfonylethyl, methylsulfinylethyl, methylthioethyl, etc., substituted or unsubstituted aromatic hydrocarbon groups such as phenyl, 4-hydroxy-3,5-dimethoxyphenyl, 3,5-di-tert-butyl-4-hydroxyphenyl, 4-dimethylaminophenyl, etc., benzyl and substituted benzyl groups such as p-nitrobenzyl, p-methoxybenzyl, 2,4-dimethoxybenzyl and so on. Aside from these groups, any of the known carboxy protecting groups can likewise be employed as the group $R^2$. Preferred examples of the group W include hydroxyl and $C_{1-6}$ alkoxy group.

Therefore, the following specific compounds may be mentioned as representative examples of compound (II').

(i) Methyl 2-methoxyimino-3-oxobutyrate
(ii) tert-Butyl 2-methoxyimino-3-oxobutyrate
(iii) 2-Methoxyimino-3-oxobutyric acid
(iv) tert-Butyl 2-ethoxycarbonylmethoxyimino-3-oxobutyrate
(v) Methyl 2-methoxyimino-3-oxothiobutyrate
(vi) 2-Methoxyimino-3-oxobutyramide
(vii) p-Nitrobenzyl 2-t-butoxycarbonylmethoxyimino-3-oxobutyrate The compound (III) is an ester or amide of a 2-(substituted)hydroxyimino-3-silyloxy-3-butenoic acid and preferred examples of compound (III) include compounds of the formula

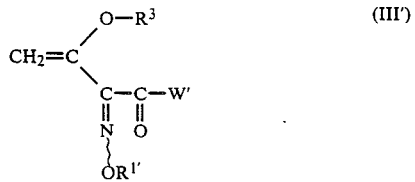

wherein $R^{1'}$ is an alkyl group which may optionally be substituted or $R^3$; W' is $OR^{2'}$, $SR^{2'}$ or

wherein $R^{2'}$ is a hydrocarbon group which may optionally be substituted or $R^3$; and $R^3$ is a trialkylsilyl group or a halodialkylsilyl group. In compound (III'), the alkyl group which may optionally be substituted as represented by $R^{1'}$ may for example be as mentioned above for $R^1$ in compound (II'). The hydrocarbon group which may optionally be substituted, as represented by $R^{2'}$, may for example be as mentioned above for $R^2$ in compound (II'). $R^3$ means a trialkylsilyl group or a halodialkylsilyl group. The trialkylsilyl group may be a tri-$C_{1-4}$ alkylsilyl group such as trimethylsilyl, triethylsilyl, tripropylsilyl, tert-butyldimethylsilyl, etc., and the halodialkylsilyl group may be a halo-di-$C_{1-4}$ alkylsilyl group such as chlorodimethylsilyl and so on. Preferred examples of the group $R^{1'}$ include a tri-$C_{1-4}$ alkylsilyl group and a $C_{1-4}$ alkyl which may optionally be substituted with a protected carboxyl group. Preferred examples of the group $R^3$ include a tri-$C_{1-4}$ alkylsilyl group. And, preferred examples of the group W' include a tri-$C_{1-4}$ alkylsilyloxy and $C_{1-6}$ alkoxy group. The following specific compounds may be mentioned as representative examples of compound (III')

(i) Methyl 2-methoxyimino-3-trimethylsilyloxy-3-butenoate
(ii) Ethyl 2-methoxyimino-3-trimethylsilyloxy-3-butenoate
(iii) tert-Butyl 2-methoxyimino-3-trimethylsilyloxy3-butenoate
(iv) Phenyl 2-methoxyimino-3-trimethylsilyloxy-3-butenoate
(v) Allyl 2-methoxyimino-3-trimethylsilyloxy-3-butenoate
(vi) Methylsulfonylethyl 2-methoxyimino-3-trimethylsilyloxy-3-butenoate
(vii) Methylsulfinylethyl 2-methoxyimino-3-trimethylsilyloxy-3-butenoate
(viii) Methylthioethyl 2-methoxyimino-3-trimethylsilyloxy-3-butenoate
(ix) Benzyl 2-methoxyimino-3-trimethylsilyloxy-3-butenoate
(x) 4-Nitrobenzyl 2-methoxyimino-3-trimethylsilyloxy-3-butenoate
(xi) 4-Methoxybenzyl 2-methoxyimino-3-trimethylsilyloxy-3-butenoate
(xii) Trimethylsilyl 2-methoxyimino-3-trimethylsilyloxy-3-butenoate
(xiii) Methyl 3-tert-butyldimethylsilyloxy-2-methoxyimino-3-butenoate
(xiv) Ethyl 3-tert-butyldimethylsilyloxy-2-methoxyimino-3-butenoate
(xv) tert-Butyl 3-tert-butyldimethylsilyloxy-2-methoxyimino-3-butenoate
(xvi) Methyl 2-methoxycarbonylmethoxyimino-3-trimethylsilyloxy-3-butenoate
(xvii) tert-Butyl 2-ethoxycarbonylmethoxyimino-3-trimethylsilyloxy-3-butenoate
(xviii) Methyl 2-p-nitrobenzyloxycarbonylmethoxyimino-3-trimethylsilyloxy-3-butenoate
(xix) Methyl 2-tert-butyloxycarbonylmethoxyimino-3-trimethylsilyloxy-3-butenoate
(xx) Methyl 3-trimethylsilyloxy-2-trimethylsilyloxycarbonylmethoxyimino-3-butenoate
(xxi) Methyl 3-trimethylsilyloxy-2-trimethylsilyloxyimino-3-butenoate
(xxii) Methyl 2-tert-butyldimethylsilyloxyimino-3-trimethylsilyloxy-3-butenoate
(xxiii) Methyl 3-chlorodimethylsilyloxy-2-methoxyimino-3-butenoate
(xxiv) tert-Butyl 3-chlorodimethylsilyloxy-2-methoxyimino-3-butenoate
(xxv) S-Methyl 2-methoxyimino-3-trimethylsilyloxy-3-butenethioate
(xxvi) S-Ethyl 3-chlorodimethylsilyloxy-2-methoxyimino-3-butenethioate The objective compound (I) is an ester or amide of a 4-halo-2-(substituted or unsubstituted)hydroxyimino-3-oxobutyric acid and preferred examples of objective compound (I) include compounds of the formula

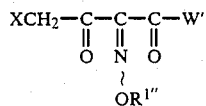  (I')

wherein X is a halogen atom; $R^{1''}$ is a hydrogen atom, an alkyl group which may optionally be substituted or $R^3$ and $R^3$ and W'are as defined hereinbefore. In compound (I'), X is a halogen atom such as fluorine, chlorine, bromine and iodine. Preferred examples of X include chlorine and bromine. Referring, further, to compound (I'), the alkyl group which may optionally be substituted represented by $R^{1''}$ may for example be as mentioned above for $R^1$ in compound (II'), and $R^3$ and W' respectively have the same meanings as $R^3$ and W' in compound (III'). Preferred examples of the group $R^{1''}$ include a hydrogen atom and a $C_{1-4}$ alkyl which may optionally be substituted with carboxyl or a protected carboxyl group. The following specific compounds may be mentioned as representative examples of compound (I').

(i) Methyl 4-bromo-2-methoxyimino-3-oxobutyrate
(ii) Methyl 4-chloro-2-methoxyimino-3-oxobutyrate
(iii) Methyl 4-iodo-2-methoxyimino-3-oxobutyrate
(iv) Ethyl 4-bromo-2-methoxyimino-3-oxobutyrate
(v) Ethyl 4-chloro-2-methoxyimino-3-oxobutyrate
(vi) tert-Butyl 4-bromo-2-methoxyimino-3-oxobutyrate
(vii) tert-Butyl 4-chloro-2-methoxyimino-3-oxobutyrate
(viii) Allyl 4-bromo-2-methoxyimino-3-oxobutyrate
(ix) Allyl 4-chloro-2-methoxyimino-3-oxobutyrate
(x) Phenyl 4-bromo-2-methoxyimino-3-oxobutyrate
(xi) Phenyl 4-chloro-2-methoxyimino-3-oxobutyrate
(xii) Methylsulfonylethyl 4-bromo-2-methoxyimino-3-oxobutyrate
(xiii) Methylsulfonylethyl 4-chloro-2-methoxyimino-3-oxobutyrate
(xiv) Methylsulfinylethyl 4-bromo-2-methoxyimino-3-oxobutyrate
(xv) Methylsulfinylethyl 4-chloro-2-methoxyimino-3-oxobutyrate
(xvi) Methylthioethyl 4-bromo-2-methoxyimino-3-oxobutyrate
(xvii) Methylthioethyl 4-chloro-2-methoxyimino-3-oxobutyrate
(xviii) Benzyl 4-chloro-2-methoxyimino-3-oxobutyrate
(xix) p-Nitrobenzyl 4-chloro-2-methoxyimino-3-oxobutyrate
(xx) p-Methoxybenzyl 4-chloro-2-methoxyimino-3-oxobutyrate
(xxi) Ethyl 4-bromo-2-ethoxycarbonylmethoxyimino-3-oxobutyrate
(xxii) Ethyl 4-chloro-2-ethoxycarbonylmethoxyimino-3-oxobutyrate
(xxiii) Methyl 4-bromo-2-tert-butoxycarbonylmethoxyimino-3-oxobutyrate
(xxiv) Methyl 4-chloro-2-tert-butoxycarbonylmethoxyimino-3-oxobutyrate
(xxv) Methyl 4-chloro-2-(4-nitrobenzyloxyimino)-3-oxobutyrate
(xxvi) Trimethylsilyl 4-chloro-2-methoxyimino-3-oxobutyrate
(xxvii) Methyl 4-chloro-2-trimethylsilyloxyimino-3-oxobutyrate
(xxviii) Methyl 4-chloro-2-(1-tert-butoxycarbonyl-1-methylethoxyimino)-3-oxobutyrate
(xxix) Methyl 4-chloro-2-methoxyimino-3-oxothiobutyrate
(xxx) Methyl 4-bromo-2-methoxyimino-3-oxothiobutyrate
(xxxi) 4-Bromo-2-methoxyimino-3-oxobutyramide
(xxxii) tert-Butyl 4-chloro-2-hydroxyimino-3- oxobutyrate Referring to the compounds (I), (II) and (III)(the formulas (I'), (II') and (III')), the 2-(substituted or unsubstituted)hydroxyimino group

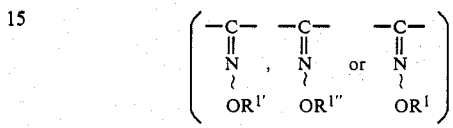

may be syn-configuration

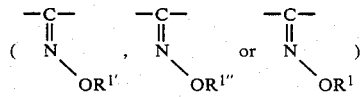

or anti-configuration

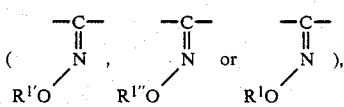

or a mixture of syn- and anti- forms, and any of the forms fall within the ambit of the present invention. And, among these forms syn form is preferred as an intermediate of value.

In accordance with the present invention, compound (III) can be produced by reacting compound (II) with a silylating agent.

When compound (II) is a free acid, i.e. 2-(substituted or unsubstituted) hydroxyimino-3-oxobutyric acid, it may be in the form of a salt with an alkali metal such as sodium, potassium, etc. or an alkaline earth metal such as calcium, etc. The silylating agent may be any one capable of converting compound (II) to compound (III). Thus, for example, halotri-$C_{1-4}$alkylsilanes such as chlorotrimethylsilane, tert-butyldimethylchlorosilane, bromotrimethylsilane, iodotrimethylsilane, etc., tri-$C_{1-4}$ alkylsilyl trifluoromethanesulfonates such as trimethylsilyl trifluoromethanesulfonate, etc., $C_{1-4}$alkyl 2-[tri-$C_{1-4}$alkylsilyl]acetates such as ethyl 2-(trimethylsilyl)acetate, etc., N,O-bistri- $C_{1-4}$alkylsilylacetamides such as N,O-bistrimethylsilylacetamide, etc., N-tri-$C_{1-4}$alkylsilylacetamides such as N-trimethylsilylacetamide, etc., hexa-$C_{1-4}$alkyldisilazanes such as hexamethyldisilazane, etc. and dihalodi-$C_{1-4}$alkylsilanes such as dichlorodimethylsilane, etc. may be used. Particularly preferred are halotri-$C_{1-4}$alkylsilanes such as chlorotrimethylsilane. The silylating agent may be used generally in a proportion of 1 to 10 moles to each mole of compound (II) and preferably in the range of 1 to 3 moles on the same basis. Where the carboxyl group of compound (II) is free or the 2-(substituted or unsubstituted)hydroxyimino group of (II) includes a hydroxyl or carboxyl group, this carboxy group or hydroxyl group reacts with a silylating agent to form a silyl ester or ether. Therefore, the silylating agent is preferably used in an excess amount for this reaction.

This silylation reaction may generally be conducted in a substantially anhydrous non-protonic organic solvent. The non-protonic solvent may be any such solvent that does not adversely affect the reaction. Thus, for example, nitriles such as acetonitrile, ethers such as tetrahydrofuran, 1,2-dimethoxyethane, dioxane, diethyl ether, etc., halogenated hydrocarbons such as methylene chloride, chloroform, carbon tetrachloride, etc., esters such as ethyl acetate, butyl acetate, etc., amides such as N,N-dimethylformamide, N,N-dimethylacetamide, etc., and hydrocarbons such as benzene, toluene, xylene, hexane, pentane, etc., as well as mixtures of such solvents may be used. Particularly preferred are nitriles such as acetonitrile and halogenated hydrocarbons such as methylene chloride. And, more preferred examples of non-protonic organic solvent may be nitriles such as acetonitrile. The used proportion of such non-protonic organic solvent is 0.2 to 20 l per mole of compound (II) and preferably 1 to 5 l on the same basis. This silylation reaction is preferably conducted in the presence of a base, e.g., tertiary amines such as trialkylamines (triethylamine, trimethylamine, tributylamine, etc.), cyclic amines (N-methylpyrolidine, N-methylpiperidine, N-methylmorpholine, pyridine, picoline, lutidine, 1,8-diazabicyclo[5,4,0]-7-undecene, 1,5-diazabicyclo[4,3,0]-5-nonene, N,N-dimethylaniline, N-methylimidazole, etc.), diamines (tetramethylethylenediamine, etc.), etc., metal amides such as lithium diisopropylamide, lithium diethylamide, lithium hexamethyldisilazide, lithium 2,2,6,6-tetramethylpiperidide, lithium dicyclohexylamide, etc., metal alkoxides such as sodium methoxide, potassium tert-butoxide, etc., metal hydrides such as sodium hydride, potassium hydride, calcium hydride, etc., and alkyl metals such as butyllithium, methyllithium, ethylmagnesium bromide, phenyllithium, sec-butyllithium, tert-butyllithium and so on. Preferred bases are tri-$C_{1-4}$alkylamines such as triethylamine and so on. Such a base may be used generally in a proportion of 1 to 10 moles to each mole of compound (II) and preferably in the range of 1 to 3 moles on the same basis. There is practically no limitation on the reaction temperature, so far as the reaction is allowed to proceed, but the reaction is conducted generally at a temperature between $-50°$ C. to $80°$ C. and preferably in the range of $0°$ C. to $30°$ C. Though it depends on the starting material (II), solvent, base, reaction temperature, etc., it is advisable to carry the reaction to completion generally in 0.2 to 6 hours and preferably in 0.5 to 3 hours. Typically, this silylation reaction may be conducted by adding 1 to 3 moles of chlorotrimethylsilane to each mole of compound (II) in acetonitrile in the presence of triethylamine and stirring the mixture at $20°$ to $25°$ C. Though it depends on other conditions, the reaction in this case usually goes to completion in 0.5 to 3 hours.

The compound (III) produced as the result of silylation can be submitted to the next halogenation reaction either after removal of the base from the reaction mixture or after isolation of the compound (III). Since the base used in the silylation reaction may, if allowed to remain, cause rehalogenation in the halogenation reaction, it is advisable to remove the base completely from the reaction mixture containing compound (III). The removal of the base or isolation of compound (III) from the reaction mixture after silylation can be accomplished by known procedures. And, the known procedures may be selected from the procedures such as concentration, concentration under reduced pressure, filtration, solvent extraction, crystallization, recrystallization, distillation, distillation under reduced pressure, sublimation, centrifugation, chromatography, membrane dialysis or the like or a suitable combination of such procedures. The use of a volatile substance such as triethylamine as the base is convenient in that it can be easily removed by concentration under reduced pressure, for instance.

In accordance with the method of the invention, the objective compound (I) can be produced by reacting compound (III) with a halogenating agent.

As compound (III), the reaction mixture obtained by the above-described production process for compound (III) can be used after removal of the base. Or the compound (III) isolated from the reaction mixture can be used. As the halogenating agent, there can be employed halogens (chlorine, bromine, iodine, etc.), sulfuryl halides (e.g. sulfuryl chloride, etc.), N-halosuccinimides (e.g. N-bromosuccinimide, N-chlorosuccinimide, etc.), 1,3-dibromo-5,5-dimethylhydantoin and so on. Particularly preferred are bromine, sulfuryl chloride and N-bromosuccinimide. Such a halogenating agent can generally serve the purpose only if used in an equimolar proportion based on compound (III) but may be used in excess (1 to 1.5 moles per mole of compound (III)). This halogenation reaction may generally be carried out in a solvent. The solvent may be any type of solvent that does not interfere with the reaction but may generally be selected from among hydrocarbons such as hexane, benzene, toluene, xylene, etc., nitriles such as acetonitrile, etc., ethers such as tetrahydrofuran isopropyl ether, dioxane, diethyl ether, etc., halogenated hydrocarbons such as methylene chloride, chloroform, carbon tetrachloride, etc., esters such as ethyl acetate, etc., ketones such as acetone, etc., and amides such as N,N-dimethylformamide, N,N-dimethylacetamide, etc., as well as a suitable mixture of such solvents. Preferred solvents may be halogenated hydrocarbons such as methylene chloride, etc., nitriles such as acetonitrile, etc. and ethers such as tetrahydrofuran, etc., There is practically no limitation on the reaction temperature, so far as the reaction is allowed to proceed, but the reaction is carried out generally at $-50°$ C. to $80°$ C. and preferably at $-30°$ C. to $20°$ C. The reaction time depends on compound (III), solvent, reaction temperature and other conditions but may generally be not more than 1 hour and preferably 1 to 30 minutes. In the case that the carboxyl or/and hydroxyl group in the compound (II) form a silyl ester or/and ether, the silyl group may be removed under this reaction condition of halogenation. The compound (I) thus produced may be provided, as it is in the form of reaction mixture, as a synthetic intermediate or may be provided after isolation and purification by known procedures such as concentration, pH adjustment, solvent extraction, crystallization, recrystallization, chromatography, etc. Compound (II) which is used as a starting compound in accordance with the present invention can for example synthesized by the processes described in Jour. Indian Chem. Soc. 42, 677-680 (1965); Yakugaku Zasshi 87 (No. 10), 1209-1211 (1967), J. Am. Chem. Soc. 60, 1328-1331 (1938), Japanese Published Unexamined Patent application No. 60-199894, GB 2148282-A and GB 2161476-A and so forth or by processes analogous thereto.

The method according to the present invention is a very useful method for industrial production of objective compound (I), for objective compound (I) can thereby be produced on an industrial scale at low cost, under mild conditions, in a short sequence, in high purity and in good yield. Therefore, in the industrial production of end products using objective compound (I) as a synthetic intermediate, the method according to the present invention can be a useful step for production of the intermediate (I). For example, the objective compound (I) produced by the method of the invention can be converted to a 7β-[2-(2-aminothiazol-4-yl)-(Z)-2-(substituted or unsubstituted) hydroxyiminoacetamido]-3-(unsubstituted or substituted)-3-cephem-4-carboxylic acid, or a salt or ester thereof, which is an aminothiazole cephalosporin having excellent antibacterial activity, by the further steps of reacting (I) with thiourea to give a (Z)-2-(substituted or unsubstituted)hydroxyimino-2-(2-aminothiazol-4-yl)acetic acid ester or amide and, after conversion thereof to a reactive derivative of its carboxyl function if necessary, reacting it with an 7-amino-3-(unsubstituted or substituted)-3-cephem-4-carboxylic acid or a salt or ester thereof, or by the further steps of converting (I) to a reactive derivative of its carboxyl function, then reacting it with an 7-amino-3-(unsubstituted or substituted)-3-cephem-4-carboxylic acid or a salt or ester thereof and finally reacting the reaction product with thiourea [Japanese Published Unexamined Patent Application No. 52-102293, No. 52-125190, No. 54-9296, No. 53-5193, U.S. Pat. No. 4098888, GB 1600735-A, GB 1600736-A, GB 2012276-B, GB 2148282-A and GB 2161476-A]. The following examples are intended to illustrate the present invention in further detail and should not be construed as delimiting the scope of the invention.

The symbols used in the examples have the following meanings.

s: singlet, br: broad, d: doublet, ABq: AB-pattern quartet, $CDCl_3$: deuteriochloroform, DMSO-$d_6$: dimethylsulfoxide-$d_6$, $D_2O$: deuterium oxide, %: weight percent.

NMR (nuclear magnetic resonance spectrum), unless otherwise indicated, represents the results of a determination at 60 MHz or 90 MHz using tetramethylsilane or sodium 4,4-dimethyl-4-silapentanesulfonate (only in cases where $D_2O$ was used as the solvent) as the internal reference, with the chemical shift values being shown in units of δ(ppm).

EXAMPLE 1

In 15 ml of acetonitrile was dissolved 795 mg of methyl 2-methoxyimino-3-oxobutyrate, followed by addition of 2.1 ml of triethylamine. Then, 1.9 ml of chlorotrimethylsilane was added dropwise with ice-cooling. The mixture was stirred at 20°–25° C. for 1 hour for silylation. The reaction mixture was concentrated under reduced pressure and the residue was suspended in 15 ml of hexane. The suspension was filtered in a nitrogen gas stream to remove insolubles. The filtrate was cooled to −30° C. and a solution of 0.8 g bromine in 2 ml methylene chloride was added dropwise until the reaction mixture began to turn reddish brown. Then, 10 ml of water was added to the mixture and after 10 minutes' stirring, the organic layer was taken and dried over anhydrous magnesium sulfate and concentrated under reduced pressure. The concentrate was then chromatographed on a silica gel column and elution was carried out with 100 ml of hexane-ether (1:1, v/v). The eluate was concentrated under reduced pressure to give 1.01 g of methyl 4-bromo-2-methoxyimino-3-oxobutyrate as colorless oil. Yield 84.9%.

NMR ($CDCl_3$): δ3.89 (3H, s), 4.15 (3H, s), 4.35 (2H, s) ppm.

EXAMPLE 2

In 15 ml of acetonitrile was dissolved 795 mg of methyl 2-methoxyimino-3-oxobutyrate, followed by addition of 2.1 ml of triethylamine. Then, 1.9 ml of chlorotrimethylsilane was added dropwise with ice-cooling and the mixture was stirred at 20°–25° C. for 1 hour for silylation. The reaction mixture was concentrated under reduced pressure and the residue was suspended in 15 ml of tetrahydrofuran. The suspension was filtered in a nitrogen gas stream to remove insolubles. The filtrate was cooled to −30° C. and 0.405 ml of sulfuryl chloride was added dropwise. After the temperature of the system was increased to 20° C., the mixture was concentrated under reduced pressure. The concentrate was chromatographed on a silica gel column and elution was carried out with 100 ml of hexane-ether (1:1, v/v). The eluate was concentrated under reduced pressure to give 813 mg of methyl 4-chloro-2-methoxyimino-3-oxobutyrate as colorless oil. Yield 84.1%.

NMR ($CDCl_3$): δ3.90(3H, s), 4.17 (3H, s), 4.63 (2H, s) ppm.

EXAMPLE 3

Following the same silylation reaction as in Example 1, the obtained reaction mixture was concentrated under reduced pressure. To the residue was added 15 ml of tetrahydrofuran and the resulting suspension was filtered in a nitrogen gas stream to remove insolubles. The filtrate was cooled to −30° C. and a solution of 1.27 g iodine in 5 ml tetrahydrofuran was added. After the temperature of the system was increased to 20° C., the reaction mixture was diluted with 5 ml of water and stirred for a while ( 10 minutes). The organic layer was taken, washed with 10 ml of 10% aqueous sodium chloride solution, dried over anhydrous magnesium sulfate, and concentrated under reduced pressure. The concentrate was chromatographed on a silica gel column and elution was carried out with 100 ml of methylene chloride. The eluate was concentrated under reduced pressure to give methyl 4-iodo-2-methoxyimino-3-oxobutyrate as colorless oil.

NMR ($CDCl_3$): δ3.86 (3H, s), 4.14 (3H, s), 4.22 (2H, s) ppm.

Elemental analysis ($C_6H_8NO_4I$):

Calcd.(%): C., 25.28; H, 2.83; N, 4.91.

Found (%): C., 25.41; H, 2.82; N, 4.96.

EXAMPLE 4

The procedure of Example 1 was repeated except that 1.00 g of tert-butyl 2-methoxyimino-3-oxobutyrate was used in lieu of 795 mg of methyl 2-methoxyimino-3-oxobutyrate. The procedure yielded 1.24 g of tert-butyl 4-bromo-2-methoxyimino-3-oxobutyrate as colorless oil. Yield 89.1%.

NMR ($CDCl_3$): δ1.54 (9H, s), 4.12 (3H, s), 4.34 (2H, s) ppm.

EXAMPLE 5

The procedure of Example 2 was repeated except that 1.00 g of tert-butyl 2-methoxyimino-3-oxobutyrate was used in lieu of 795 mg of methyl 2-methoxyimino-3- oxobutyrate. The procedure yielded 1.06 g of tert-butyl 4-chloro-2-methoxyimino-3-oxobutyrate as colorless oil. Yield 90.5%.

NMR (CDCl$_3$): δ1.56 (9H, s), 4.15 (3H, s), 4.60 (2H, s) ppm.

EXAMPLE 6

Following the silylation reaction as in Example 1, 10 ml of xylene was added to the obtained reaction mixture and the mixture was concentrated under reduced pressure. The residual solution was suspended in 15 ml of hexane and the suspension was filtered in a nitrogen gas stream to remove insolubles. The filtrate was cooled to −30° C. and a solution of 0.8 g bromine in 2 ml methylene chloride was added dropwise until the reaction mixture began to turn reddish brown. Then, 10 ml of water was added to the mixture and after 10 minutes' stirring, the organic layer was taken and dried over anhydrous magnesium sulfate and concentrated under reduced pressure. To the residue was added 10 ml of tetrahydrofuran, followed by addition of a solution of 761 mg thiourea and 2.04 g sodium acetate trihydrate in 10 ml water. The mixture was stirred at 20°–25° C. for 30 minutes, after which it was extracted with 10 ml portions of ethyl acetate twice. The organic extracts were combined, washed with 10 ml of 5% aqueous sodium hydrogen carbonate solution and 10 xl of water in that order, dried over anhydrous magnesium sulfate, and concentrated under reduced pressure. The precipitate was collected by filtration, washed with a small amount (2 ml) of xylene and dried under reduced pressure. The above procedure gave 875 mg of methyl 2-(2-aminothiazol-4-yl)-(Z)-2-methoxyiminoacetate as crystalline powder. Yield 81.4%.

NMR (DMSO-d$_6$) δ3.75 (3H, s), 3.82 (3H, s), 6.83 (1H, s), 7.13 (2H, br. s).

EXAMPLE 7

Following the same silylation reaction as in Example 1, 10 ml of xylene was added to the obtained reaction mixture and the mixture was concentrated under reduced pressure. The residue was suspended in 15 ml of tetrahydrofuran and the suspension was filtered in a nitrogen gas stream to remove insolubles. The filtrate was cooled to 0°–5° C. and 890 mg of N-bromosuccinimide was added in small portions, followed by 30 minutes' stirring at the same temperature. The reaction mixture was washed twice with 10 ml portions of 5% aqueous sodium hydrogen carbonate solution, further washed with 10 ml of 10% aqueous sodium chloride solution, dried over anhydrous magnesium sulfate, and concentrated under reduced pressure. To the residue was added 10 ml of tetrahydrofuran, followed by addition of a solution of 761 mg thiourea and 2.04 g sodium acetate trihydrate in 10 ml water. The mixture was stirred at 20°–25° C. for 30 minutes. Thereafter, the reaction mixture was worked up in the same manner as described in Example 6 to give 825 mg of methyl 2-(2-aminothiazol-4-yl)-(Z)-2-methoxyiminoacetate as crystalline powder. Yield 76.7%.

The NMR spectrum of this product was in agreement with that of the compound obtained in Example 6.

EXAMPLE 8

Following the same silylation reaction as in Example 1, 10 ml of xylene was added to the obtained reaction mixture and the mixture was concentrated under reduced pressure. The residue was suspended in 15 ml of tetrahydrofuran and the suspension was filtered in a nitrogen gas stream to remove insolubles. The filtrate was cooled to −30° C. and 0.45 ml of sulfuryl chloride was added dropwise. After the temperature was increased to 20° C., the mixture was concentrated under reduced pressure. Tarry matter was removed from the residue and 30 ml of tetrahydrofuran was added to the supernatant, followed by addition of a solution of 761 mg thiourea and 2.04 g sodium acetate trihydrate in 30 ml water. The mixture was stirred with warming at 50°–60° C. for 4 hours. After cooling to 20° C., the reaction mixture was worked up in the same manner as Example 6 to give 850 mg of methyl 2-(2-aminothiazol-4-yl)-(Z)-2-methoxyiminoacetate as crystalline powder. Yield 79.1%.

The NMR spectrum of this product was in good agreement with that of the compound obtained in Example 6.

EXAMPLE 9

In 15 ml of acetonitrile was dissolved 1.00 g of tert-butyl 2-methoxyimino-3-oxobutyrate, followed by addition of 2.1 ml of triethylamine. Then, 1.9 ml of chlorotrimethylsilane was added dropwise with ice-cooling and the mixture was stirred at 20°–25° C. for 1.5 hours for silylation. The reaction mixture was concentrated under reduced pressure and the residue was suspended in 15 ml of hexane. The suspension was filtered in a nitrogen gas stream to remove insolubles. The filtrate was cooled to −30° C. and a solution of 0.8 g bromine in 2 ml methylene chloride was added dropwise until the reaction mixture began to turn reddish brown. After 10 ml of water was added and the mixture was stirred for a while (10 minutes), the organic layer was separated, dried over anhydrous magnesium sulfate and concentrated under reduced pressure. To the residue was added 10 ml of trifluoroacetic acid and the mixture was stirred at 20°–25° C. for 40 minutes for de-esterification. The reaction mixture was then concentrated under reduced pressure. The concentrate was crystallized from 3 ml of carbon tetrachloride and the crystals were collected by filtration and dried under reduced pressure. The above procedure yielded 785 mg of 4-bromo-2-methoxyimino-3-oxobutyric acid as crystalline powder. Yield 70.5%.

NMR (CDCl$_3$): δ4.19 (3H, s), 4.39 (2H, s), 9.4 (1H, br. s) ppm.
IR(KBr): 2930, 1735, 1710, 1595, 1045 cm$^{-1}$
Elemental analysis (C$_5$H$_6$NO$_4$Br):
Calcd.(%): C., 26.81; H, 2.70; N, 6.25.
Found (%): C., 27.16; H, 2.61; N, 6.37.

EXAMPLE 10

Following the same silylation reaction as in Example 9, 10 ml of xylene was added to the obtain reaction mixture and the mixture was concentrated under reduced pressure. To the residue was added 15 ml of tetrahydrofuran and the resulting suspension was filtered in a nitrogen gas stream to remove insolubles. The filtrate was cooled to −30° C. and 0.405 ml of sulfuryl chloride was added dropwise. After the temperature of the system was increased to 20° C., the reaction mixture was concentrated under reduced pressure. Tarry matter was removed from the concentrate and 10 ml of trifluoroacetic acid was added to the supernatant under ice-cooling. The mixture was stirred at 20°–25° C. for 40 minutes, after which it was concentrated under reduced pressure. The residue was diluted with 20 ml of water and adjusted to pH 9.0 by dropwise addition of 20% aqueous sodium hydroxide solution. The mixture was washed twice with 20 ml portions of methylene chloride and the aqueous layer was taken and adjusted to pH 0.5 by dropwise addition of concentrated hydrochloric acid. This aqueous layer was saturated with sodium chloride and extracted 3 times with 20 ml portions of ether. The organic extracts were combined, dried over anhydrous magnesium sulfate and concentrated under reduced pressure. The concentrate was crystallized from 5 ml of carbon tetrachloride-methylene chloride (3:2) and the resulting crystals were collected by filtration and dried under reduced pressure. The above procedure yielded 670 mg of 4-chloro-2-methoxyimino-3-oxobutyric acid as crystalline powder. Yield 75.1%..

NMR (CDCl$_3$): δ6 4.23 (3H, s), 4.65 (2H, s), 9.1 (1H, br. s) ppm.

IR (KBr): 3000, 1730, 1705, 1600, 1040 cm$^{-1}$.

Elemental analysis ($C_5H_6NO_4Cl$):

Calcd (%) C., 33.45; H, 3.37; N, 7.80.

Found (%): C., 33.31; H, 3.30; N, 7.95.

EXAMPLE 11

In 15 ml of acetonitrile was dissolved 725 mg of 2-methoxyimino-3-oxobutyric acid, followed by addition of 2.8 ml of triethylamine. Then, 2.5 ml of chlorotrimethylsilane was added dropwise with ice-cooling and the mixture was stirred at 20°-25° C. for 2 hours. After addition of 10 ml of xylene, the reaction mixture was concentrated under reduced pressure and the residue was suspended in 15 ml of tetrahydrofuran. The suspension was filtered in a nitrogen gas stream to remove insolubles. This filtrate containing trimethylsilyl 2-ethoxyimino-3-oxobutyrate trimethylsilyl enol ether (i.e. trimethylsilyl 2-methoxyimino-3-trimethylsilyloxy-3-butenoate) was cooled to −30° C. and 0.45 ml of sulfuryl chloride was added dropwise thereto. After the temperature of the mixture was increased to 20° C., the reaction mixture was concentrated under reduced pressure and the residue was diluted with 20 ml of water and stirred for 10 minutes for hydrolyzing the trimethylsilyl ester. Then, 2N aqueous sodium hydroxide solution was added dropwise to adjust the reaction mixture to pH 9.0. The reaction mixture was washed twice with 20 ml portions of methylene chloride and the aqueous layer was adjusted to pH 0.5 by dropwise addition of concentrated hydrochloric acid. The aqueous layer was saturated with sodium chloride and extracted 3 times with 20 ml portions of ether. The organic layers were combined, dried over anhydrous magnesium sulfate and concentrated under reduced pressure. The above procedure gave 4-chloro-2-methoxyimino-3-oxobutyric acid.

EXAMPLE 12

In 15 ml of acetonitrile was dissolved 795 mg of methyl 2-methoxyimino-3-oxobutyrate, followed by addition of 2.1 ml of triethylamine. Then, 1.9 ml of chlorotrimethylsilane was added dropwise with ice-cooling and the mixture was stirred at 20°-25° C. for 1 hour for silylation. The reaction mixture was concentrated under reduced pressure and the residue was suspended in 10 ml of carbon tetrachloride and the suspension was filtered in a nitrogen gas stream to remove insolubles. The filtrate was concentrated under reduced pressure to give 1.00 g of methyl 2-methoxyimino-3-trimethylsilyloxy-3-butenoate as oil. Yield 86.5%.

NMR (CCl$_4$): δ0.21 (9H, s), 3.85 (3H, s), 3.98 (3H, s), 4.63 (2H, br. s) ppm.

EXAMPLE 13

The procedure of Example 12 was repeated except that 1.06 g of tert-butyl 2-methoxyimino-3-oxobutyrate was used in lieu of 795 mg of methyl 2-methoxyimino-3-oxobutyrate. The procedure yielded 1.27 g of tert-butyl 2-methoxyimino-3-trimethylsilyloxy-3-butenoate as oil. Yield 88.2%.

NMR (CCl$_4$): δ0.22 9H, s), 3.93 (3H, s), 4.58 and 4.64 (2H, ABq, J=2 Hz) ppm.

EXAMPLE 14

In 20 ml of acetonitrile were dissolved 795 mg of methyl 2-methoxyimino-3-oxobutyrate and 2.25 g of sodium iodide, followed by addition of 2.1 ml of triethylamine. Then, a solution of 1.13 g tert-butyldimethylchlorosilane in 10 ml acetonitrile was added dropwise and the mixture was refluxed for 6.5 hours. The reaction mixture was concentrated under reduced pressure and 20 ml of hexane and 20 ml of water were added to dissolve the residue. The organic layer was separated, washed with 20 ml of 5% aqueous sodium hydrogen carbonate solution, 20 ml of 1N hydrochloric acid and 20 ml of water in the order mentioned, dried over anhydrous magnesium sulfate, and concentrated under reduced pressure. The residue was chromatographed on a silica gel column and elution was carried out with 100 ml of hexane-ether (5:1, v/v). The eluate was concentrated under reduced pressure to give methyl 3-tert-butyldimethylsilyloxy-2-methoxyimino-3-butenoate as oil.

NMR (CDCl$_3$): δ0.18 (6H, s), 0.93 (9H, s), 3.85 (3H, s), 3.96 (3H, s), 4.67 (2H, s) ppm.

EXAMPLE 15

The procedure of Example 2 was repeated except that 1.37 g of tert-butyl 2-ethoxycarbonylmethoxyimino-3-oxobutyrate was used in lieu of 795 mg of methyl 2-methoxyimino-3-oxobutyrate. The procedure gave 1.33 g of tert-butyl 4-chloro-2-ethoxycarbonylmethoxyimino-3-oxobutyrate as colorless oil. Yield 86.2%.

NMR (CDCl$_3$): δ1.31 (3H, t, J=7 Hz), 1.56 (9H, s), 4.27 (2H, q, J=7 Hz), 4.54 (2H, s), 4.76 (2H, s) ppm.

EXAMPLE 16

In 15 ml of acetonitrile was dissolved 1.07 g of tert-butyl 2-hydroxyimino-3-oxobutyrate, followed by addition of 2.8 ml of triethylamine. Then, 2.5 ml of chlorotrimethylsilane was added dropwise with ice-cooling and the mixture was stirred at 20°-25° C. for 1.5 hours, after which it was concentrated under reduced pressure. The residue was suspended in 15 ml of tetrahydrofuran and the suspension was filtered in a nitrogen gas stream to remove insolubles. This filtrate containing tert-butyl 2-trimethylsilyloxyimino-3-trimethylsilyloxy-3-butenoate was cooled to −30° C. and 0.46 ml of sulfuryl chloride was added dropwise. After the temperature of the system was increased to 20° C., the reaction mixture was concentrated under reduced pressure. The concentrate was chromatographed on a silica gel column and elution was carried out with 100 ml of hexane-ether (1:1, v/v). The eluate was concentrated under reduced pressure to give 1.08 g of tert-butyl 4-chloro-2-hydroxyimino-3-oxobutyrate. Yield 85.2%.

NMR (CDCl$_3$): δ1.51 9H, s), 4.50 (2H, s) ppm

REFERENCE EXAMPLE 1

(1) In 15 ml of methylene chloride was dissolved 2.02 g of 4-bromo-2-methoxyimino-3-oxobutyric acid, followed by addition of 2.06 g of phosphorus pentachloride in small portions at 0°–5° C. The mixture was stirred at the same temperature for 5 minutes and, then, at 20°–25° C. for 1 hour, after which it was concentrated under reduced pressure. To the residue was added 20 ml of hexane and the mixture was stirred for a while and allowed to stand. The supernatant was concentrated under reduced pressure to give 2.1 g of 4-bromo-2-methoxyimino-3-oxobutyryl chloride as oil. Yield 96%.

NMR (CDCl$_3$): δ4.18 (3H, s), 4.29 (2H, s) ppm.

(2) In a solvent mixture of 50 ml water and 35 ml tetrahydrofuran were dissolved 1.64 g of 7β-amino-3-(1-methyl-1H-tetrazol-5-yl)thiomethyl-3-cephem-4-carboxylic acid and 1.68 g of sodium hydrogen carbonate. To this solution was added a solution of 2.1 g 4-bromo-2-methoxyimino-3-oxobutyryl chloride in 15 ml tetrahydrofuran and the mixture was stirred at 20°–25° C. for 5 minutes. Then, a solution of 1.52 g thiourea in 20 ml water was added thereto and the mixture was stirred at the same temperature for 1 hour. The reaction mixture was adjusted to pH 7.0 with 20% aqueous sodium carbonate solution and concentrated under reduced pressure. The concentrate was subjected to column chromatography using Diaion HP-40 (Mitsubishi Chemical Industries, Ltd.) and elution was carried out with 400 ml of water-isopropyl alcohol (9:1, v/v). The eluate was lyophilized to give 2.35 g of sodium 7β-[2-(2-aminothiazol-4-yl)-(Z)-2-methoxyiminoacetamido]-3-(1-methyl-1H-tetrazol-5-yl)thiomethyl-3-cephem-4-carboxylate. Yield 88.2%. Analysis by high-performance liquid chromatography showed that the proportion of the (E)-isomer was not more than 1% of the (Z)-isomer.

NMR (D$_2$O): δ3.43 and 3.79 (2H, ABq, J=18 Hz), 3.95 (3H, s), 3.98 (3H, s), 4.02 and 4.32 (2H, ABq, J=14 Hz), 5.13 (1H, d, J=5 Hz), 5.72 (1H, d, J=5 Hz), 6.92 (1H, s) ppm.

REFERENCE EXAMPLE 2

The procedure of Reference Example 1 (2) was repeated using 1.65 g of 7β-amino-3-(1,2,3-thiadiazol-5-yl)thiomethyl-3-cephem-4-carboxylic acid to give 2.24 g of sodium 7β-[2-(2-aminothiazol-4-yl)-(Z)-2-methoxyiminoacetamido]-3-(1,2,3-thiadiazol-5-yl)-thiomethyl-3-cephem-4-carboxylate. Yield 83.8%. Analysis by high performance liquid chromatography showed that the proportion of the (E)-isomer was not more than 1% of the (Z)-isomer.

NMR (D$_2$O): δ3.37 and 3.72 (2H, ABq, J=18 Hz), 3.95 (3H, s), 3.92 and 4.33 (2H, ABq, J=14 Hz), 5.13 (1H, d, J=5 Hz), 5.71 (1H, d, J=5 Hz), 6.92 (1H, s), 8.59 (1H, s) ppm.

What we claim is:

1. A method of producing a compound of the formula:

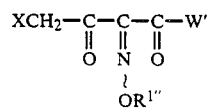

wherein

X is a halogen atom,

R$^{1''}$ is a hydrogen atom, a C$_{1-4}$ alkyl which may be substituted with one or two groups selected from carboxyl, protected carboxyl, C$_{3-6}$ cycloalkyl and a nitrogen-containing 5-membered heterocyclic group, or R$^3$, W' is OR$^{2'}$, SR$^{2'}$ or

wherein R$^{2'}$ is a hydrocarbon group which may be substituted with one or two groups selected from C$_{1-4}$ alkylsulfonyl, C$_{1-4}$ alkylsulfinyl, C$_{1-4}$ alkylthio, C$_{3-6}$ cycloalkyl, hydroxyl, nitro, C$_{1-4}$ alkoxy, di-C$_{1-4}$ alkylamino and C$_{1-4}$ alkyl groups or R$^3$, and R$^3$ is a tri-C$_{1-4}$-alkylsilyl or halodi-C$_{1-4}$-alkylsilyl group, characterized by reacting a compound of the formula:

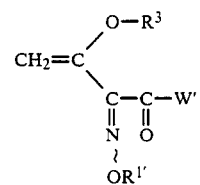

wherein R$^{1'}$, is a C$_{1-4}$ alkyl which may be substituted with one or two groups selected from carboxyl, protected carboxyl, C$_{3-6}$ cycloalkyl and nitrogen-containing 5-membered heterocyclic group, or R$^3$ and W' and R$^3$ are as defined above with a halogenating agent.

2. A method of producing a compound of the formula:

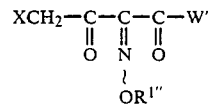

wherein X, R$^{1''}$ and W' are as defined in claim 1, characterized by reacting a compound of the formula:

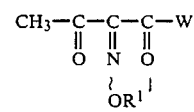

wherein R$^1$ is a hydrogen atom or a C$_{1-4}$ alkyl which may be substituted with one or two groups selected from carboxyl, protected carboxyl, C$_{3-6}$ cycloalkyl and nitrogen-containing 5-membered heterocyclic group and W is OR$^2$, SR$^2$ or

wherein R$^{2'}$ is a hydrogen atom or a hydrocarbon group which may be substituted with one or two groups selected from C$_{1-4}$ alkylsulfonyl, C$_{1-4}$ alkylsulfinyl, C$_{1-4}$ alkoxy, di-C$_{1-4}$ alkylamino and C$_{1-4}$ alkyl group, with a silylating agent and reacting the resulting compound of the formula:

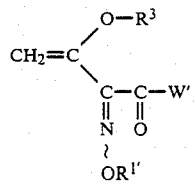

wherein $R^{1'}$, $R^3$ and $W'$, are as defined in claim 1, with a halogenating agent.

3. A method according to claim 1, wherein the halogen atom is chlorine or bromine.

4. A method according to claim 1, wherein $W'$ is a tri-$C_{1-4}$alkylsilyloxy or $C_{1-6}$alkoxy group.

5. A method according to claim 1, wherein $R^3$ is a tri-$C_{1-4}$alkylsilyl group.

6. A method according to claim 1, wherein $R^{1'}$ is a tri-$C_{1-4}$alkylsilyl group or a $C_{1-4}$alkyl which may optionally be substituted with a protected carboxyl group.

7. A method according to claim 1, wherein $W'$ is a tri-$C_{1-4}$alkylsilyloxy or $C_{1-6}$alkoxy group.

8. A method according to claim 1, wherein $R^3$ is a tri-$C_{1-4}$alkylsilyl group.

9. A method according to claim 1, wherein $R^1$ is a hydrogen atom or a $C_{1-4}$alkyl which may optionally be substituted with carboxyl or a protected carboxyl group.

10. A method according to claim 1, wherein W is hydroxyl or $C_{1-6}$ alkoxy group.

11. A method according to claim 1, wherein the silylation reaction is conducted in a nitrile.

12. A method according to claim 11, wherein the nitrile is acetonitrile.

13. A compound of the formula:

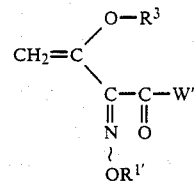

wherein $R^{1'}$ is an alkyl group which may optionally be substituted or $R^3$, $W'$ is $OR^{2'}$, $SR^{2'}$ or

wherein $R^{2'}$ is a hydrocarbon group which may optionally be substituted or $R^3$, and $R^3$ is a trialkylsilyl or halodialkylsilyl group.

14. A compound as claimed in claim 13, wherein $R^{1'}$ is a tri-$C_{1-4}$alkylsilyl group or a $C_{1-4}$alkyl which may optionally be substituted with a protected carboxyl group.

15. A compound as claimed in claim 13, wherein $W'$ is a tri-$C_{1-4}$alkylsilyloxy or $C_{1-6}$alkoxy group.

16. A compound as claimed in claim 13, wherein $R^3$ is a tri-$C_{1-4}$alkylsilyl group.

* * * * *

Disclaimer 4,845,257.—*Kenzo Naito*, Kyoto; *Yukio Ishibashi*, Osaka, both of Japan. 4-HALOGENO-2-OXYIMINO-3-OXOBUTYRIC ACIDS AND DERIVATES. Patent dated July 4, 1989. Disclaimer filed Sept. 12, 1990, by the assignee, Takeda Chemical Industries, Ltd.

Hereby enters this disclaimer to claims 13-16 of said patent.
[ *Official Gazette Nov. 20, 1990* ]